United States Patent
Wadman

(10) Patent No.: US 8,462,356 B2
(45) Date of Patent: Jun. 11, 2013

(54) APPARATUS AND METHOD FOR OBSERVING THE SURFACE OF A SAMPLE

(75) Inventor: Sipke Wadman, Eindhoven (NL)

(73) Assignee: Koninnklijke Philips Electronics N.V., Eindhoven (NL)

( * ) Notice: Subject to any disclaimer, the term of this patent is extended or adjusted under 35 U.S.C. 154(b) by 493 days.

(21) Appl. No.: 12/679,356

(22) PCT Filed: Sep. 22, 2008

(86) PCT No.: PCT/IB2008/053832
§ 371 (c)(1),
(2), (4) Date: Mar. 22, 2010

(87) PCT Pub. No.: WO2009/040716
PCT Pub. Date: Apr. 2, 2009

(65) Prior Publication Data
US 2010/0208050 A1 Aug. 19, 2010

(30) Foreign Application Priority Data

Sep. 24, 2007 (EP) .................................... 07117032

(51) Int. Cl.
*G01B 11/30* (2006.01)
*G01B 11/24* (2006.01)

(52) U.S. Cl.
USPC ........ 356/609; 356/624; 348/77; 348/208.12; 348/326; 348/345; 396/79; 396/82; 396/107; 396/121

(58) Field of Classification Search
USPC .............. 348/63–65, 68, 77, 78, 208.12, 326, 348/345; 356/73, 600, 609, 624; 396/72, 396/79, 80, 82, 89, 102, 121, 124
See application file for complete search history.

(56) References Cited

U.S. PATENT DOCUMENTS

| | | | |
|---|---|---|---|
| 5,406,342 A * | 4/1995 | Jongsma | 351/212 |
| 5,893,364 A | 4/1999 | Haar et al. | |
| 6,024,449 A * | 2/2000 | Smith | 351/212 |
| 6,032,071 A | 2/2000 | Binder | |
| 6,069,689 A * | 5/2000 | Zeng et al. | 356/73 |
| 6,088,087 A | 7/2000 | Graves et al. | |
| 6,251,070 B1 | 6/2001 | Khazaka | |
| 2002/0016533 A1 | 2/2002 | Marchitto et al. | |
| 2002/0091322 A1 | 7/2002 | Chaiken et al. | |
| 2004/0169864 A1 | 9/2004 | Carl | |

(Continued)

FOREIGN PATENT DOCUMENTS

| | | |
|---|---|---|
| FR | 2821152 A | 8/2002 |
| JP | 2004321793 A | 11/2004 |

(Continued)

*Primary Examiner* — Sath V Perungavoor
*Assistant Examiner* — Nathnael Aynalem

(57) ABSTRACT

An apparatus for observing the optical appearance of a surface (2) of a sample (1) of semitransparent material, in particular the surface (2) of a human skin, the apparatus comprising a light source (11,12,13,16,17) for illuminating at least a region of interest of the surface (2) of the sample (1) from a predetermined direction, a camera (14) for observing a response to the illumination of the region of interest and an optical focus device (21,31) for determining if the camera (14) is in focus with the surface (2) of the region of interest. The invention also relates to a method for observing the optical appearance of the surface (2) of a sample (1) of semitransparent material, in particular the surface (2) of a human skin.

12 Claims, 4 Drawing Sheets

U.S. PATENT DOCUMENTS

| | | |
|---|---|---|
| 2004/0218810 A1 | 11/2004 | Momma |
| 2006/0002518 A1* | 1/2006 | Wille et al. .................. 378/207 |
| 2006/0056661 A1 | 3/2006 | Einighammer et al. |
| 2006/0092315 A1 | 5/2006 | Payonk et al. |
| 2006/0239547 A1 | 10/2006 | Robinson et al. |

FOREIGN PATENT DOCUMENTS

| | | |
|---|---|---|
| WO | 2006091781 A1 | 8/2006 |
| WO | 2007072403 A1 | 6/2007 |
| WO | 2009040732 A1 | 4/2009 |

* cited by examiner

APPARATUS AND METHOD FOR OBSERVING THE SURFACE OF A SAMPLE

FIELD OF THE INVENTION

The invention is related to an apparatus and method for observing the optical appearance of the surface of a sample of semitransparent material, in particular the surface of a human skin.

BACKGROUND OF THE INVENTION

In order to observe the optical appearance of the surface of a sample, the surface can be viewed from a certain direction, whereby a light beam is directed to the surface from another direction. Thereby, a variety of information about the surface can be obtained, depending on the direction, intensity and color of the incoming and outgoing light and on the direction of viewing towards the surface. The observed appearance may include the texture and/or relief or protrusions or projections of the surface such as hair on the skin and, in case the material of the surface itself is more or less translucent, the texture and/or color and/or morphology underneath the surface, i.e. the sub-surface. The observation can be recorded and/or analyzed.

It should be noted that the expression appearance is used in this description for each combination of aspects and/or properties of the surface of the sample and the perception of the observer of it, including the from and relief of the surface, the color of the surface, the light reflecting and light absorbing properties of the surface, etc. Observing is a general expression, it may include inspecting and/or recording and/or analyzing of the appearance of the surface.

A non-contact and non-perturbing monitoring technique is useful in many areas of technology to determine surface and/or sub-surface morphology. Furthermore, the type and density of material defects or other features, which have a geometric shape or optical perturbation, can be characterized using this technique. Another use of this technique is the analysis of the characteristics and condition of human skin.

In particular when details of the morphology are to be analyzed, it is desired to make observations of the appearance of the surface from different directions, whereby the light source also may illuminate the surface from one or more predetermined directions (different angles with respect to the plane of the surface).

In particular when the surface of a relative large object has to be observed, for example a piece of the skin of a human body, it is not possible to place the sample inside the apparatus. In that case, the apparatus should be placed on or against the sample or a part of the sample, whereby the location of the surface to be observed is at the outer side of the apparatus.

An optical measurement device for measuring an optical appearance of a surface of a sample, in particular the human skin, is disclosed in WO 2007/072403. The disclosed device comprises an illumination device for illuminating the surface with an illumination beam and a detection device for detecting the response of the sample to the illumination beam.

In the known optical measurement device a base plate is placed on a part of the sample, for example a part of the human skin, thereby touching and applying a pressure to the human skin. The part of the deformable skin, which adjoins the region on which the pressure is applied, will tend to bulge. This causes spurious reflections from the surface of the skin and causes the surface of the skin to be outside the depth of focus of the detection device which reduces the quality of the observance of the optical appearance of the surface of the sample. This disturbs the observance of appearance of the surface of the skin, because a camera, which is used to analyze the response of the human skin to the illumination beam, will produce a blurred and out-of-focus image. Furthermore, the applied pressure on the skin alters the appearance of the skin. Blood vessels are at least partly closed off, thus causing blood to drain from the skin locally and accumulate on other places, which causes red or white discolorizations of the skin.

SUMMARY OF THE INVENTION

It is an object of the invention to provide an apparatus and method for observing the optical appearance of the surface of a sample of a semitransparent material, in particular the human skin, wherein the influence of the mechanical contact of the apparatus with the surface of the sample on the quality of the observance of the optical appearance is minimized. The invention is defined by the independent claims. Advantageous embodiments are defined by the dependent claims.

This object is achieved by an apparatus according to the invention for observing the optical appearance of the surface of a sample of semitransparent material, in particular a human skin, which comprises a light source for illuminating at least a region of interest of the surface of the sample from a predetermined direction, a camera for observing a response to the illumination of the region of interest and an optical focus device for determining if the camera is in focus with at least a part of the surface of the region of interest. In this way it is safeguarded that the camera for observing the optical appearance of the surface of the sample is in focus with at least a part of the surface of the sample. The optical focus device provides that the surface of the sample is optimally focused with respect to the camera even in the case that a deformable surface, such as the human skin, is deformed by a mechanical contact of a part of the apparatus with the surface of the sample. Hence, the influence of the deformation of the surface of the sample on the quality of the observance of the optical appearance of the sample is minimized, because the optical focus device safeguards that at least a part of the surface of the sample is in focus with the camera. The invention therefore minimizes the occurrence of an observation in which the surface of the sample is not in focus with the camera resulting in a low quality observance and an out-of-focus camera setting.

In an embodiment of the apparatus according to the invention, the optical focus device comprises a focus light beam which projects a focus image on the surface of the region of interest. The focus light beam advantageously provides for an image on the surface of the sample which is used to determine if the camera is in focus with the surface of the sample. For example, the focus light beam is projected on the surface of the sample as a point spot. In another example, a collimated light beam generates a grid pattern which is projected on the surface of the region of interest, such as a laser combined with a holographic grating which projects the grid pattern on the surface of the sample. Preferably the focus light beam comprises blue light. This has the advantage that the signal to noise ratio in the observing camera is high, because blue light has a high contrast with skin color. This minimizes the influence of the focus light beam on the image, because blue light does not penetrate the sample too deep to blur the image captured by the camera.

In a preferred embodiment of the apparatus according to the invention, the optical focus device provides for a first and a second focus light beam having a first and a second angle of incidence with the surface, wherein the first angle of incidence is different from the second angle of incidence, and wherein the first and second focus light beam provide for a superposition of a first and a second image of a first and a second mask pattern on the surface of the region of interest and wherein the focus is determined by the alignment of the first and the second mask pattern image. The superposition of the first and the second mask pattern images provides for an easy assessment of the focus situation, viz. is the surface of the sample in or out of focus with respect to the camera. The mask patterns are imaged on the surface of the sample in such a way that, when the mask pattern images are aligned with respect to each other, the surface of the sample is in focus with the camera. The mask patterns can have any shape, for example rectangular or circular, or they can have specific alignment features. Furthermore, if the surface of the sample is not normal to a viewing direction, this is indicated by a distortion of the superposed images. A displacement of the superposed images is observed if the camera has an observance direction that is not perpendicular to the superposed images.

In a preferred embodiment of the apparatus according to the invention, means are provided for measuring the alignment of the superposed first and second mask pattern images. This advantageously provides for an automatic determination of the focus situation instead of a visual inspection of the alignment by an operator. For example, the high frequency contents of the superposed mask pattern images may be analyzed.

In an embodiment of the apparatus according to the invention, the optical focus device triggers the illumination of the region of interest and the observance of the response to the illumination of the region of interest when the camera is in focus with the surface of the region of interest. This automatically safeguards that the measurement or observance of the optical appearance of the sample is started only when the camera is in focus with the surface of the sample.

In an embodiment of the apparatus according to the invention, the apparatus further comprises a deformable contact ring for contacting the surface of the sample on a specific distance from the region of interest and for protecting the surface of the sample from environmental light. The deformable contact ring, such as a bellows or a soft foam part, provides for a reduction of the pressure applied to the surface of the sample, because it is deformable and flexible and hence will apply less pressure than a solid contact surface. In this way deformation of a deformable surface is reduced and, in the case of human skin, the discolorization caused by the applied pressure is also reduced. The deformable contact ring further shuts off any unwanted light from the environment which advantageously contributes to the quality of the observance of the surface of the sample.

In an embodiment of the apparatus according to the invention, the deformable contact ring comprises means for indicating that the deformable contact ring has been used. This advantageously prevents that the deformable contact ring, that contacts the surface of the sample, such as for example the human skin, is used more than once thereby reducing the risk of cross-contamination between different samples. In another embodiment the means for indicating that the deformable contact ring has been used comprises a visual indicator for contaminants. This visual indicator advantageously provides for a warning of a contaminated deformable contact ring. By replacing the deformable contact ring when it is contaminated, as is indicated by the visual indicator according to the invention, any cross-contamination between different samples is prevented.

The object is also achieved by a method for observing the optical appearance of a surface of a sample of semitransparent material, in particular the surface of a human skin, according to the invention, wherein the method comprises the steps of:

determining with an optical focus device if a camera, which is on a fixed relative position to the optical focus device, is in focus with the surface of a region of interest by changing the distance between the camera, the optical focus device and the surface;

illuminating at least a region of interest of the surface of the sample from a predetermined direction with a light source when the camera is in focus with the surface of the region of interest; and observing a response to the illumination of the region of interest with the camera.

In this way it is safeguarded that the camera for observing the optical appearance of the surface of the sample is in focus with the surface of the sample before the observance of the sample starts.

In a preferred embodiment of the method according to the invention, the method further comprises the step of contacting the surface of the sample on a specific distance from the region of interest with a deformable contact ring before the step of determining the focus, thereby protecting the surface of the sample from environmental light. The deformable contact ring, such as a bellows or a soft foam part, provides for a reduction of the pressure applied to the surface of the sample, because it is deformable and flexible and hence will apply less pressure than a solid contact surface. In this way deformation of a deformable surface is reduced and, in the case of human skin, the discolorization caused by the applied pressure is also reduced. The deformable contact ring further shuts off any unwanted light from the environment which advantageously contributes to the quality of the observance of the surface of the sample.

BRIEF DESCRIPTION OF THE DRAWINGS

These and other aspects of the invention will be further elucidated and described with reference to the drawings, in which.

The Figures are not drawn to scale. The figures are only schematic and diagrammatic representations, showing only parts of the apparatus that are relevant for the elucidation of the invention. In general, identical components are denoted by the same reference numerals in the Figures.

DETAILED DESCRIPTION OF EMBODIMENTS

Figure 1:
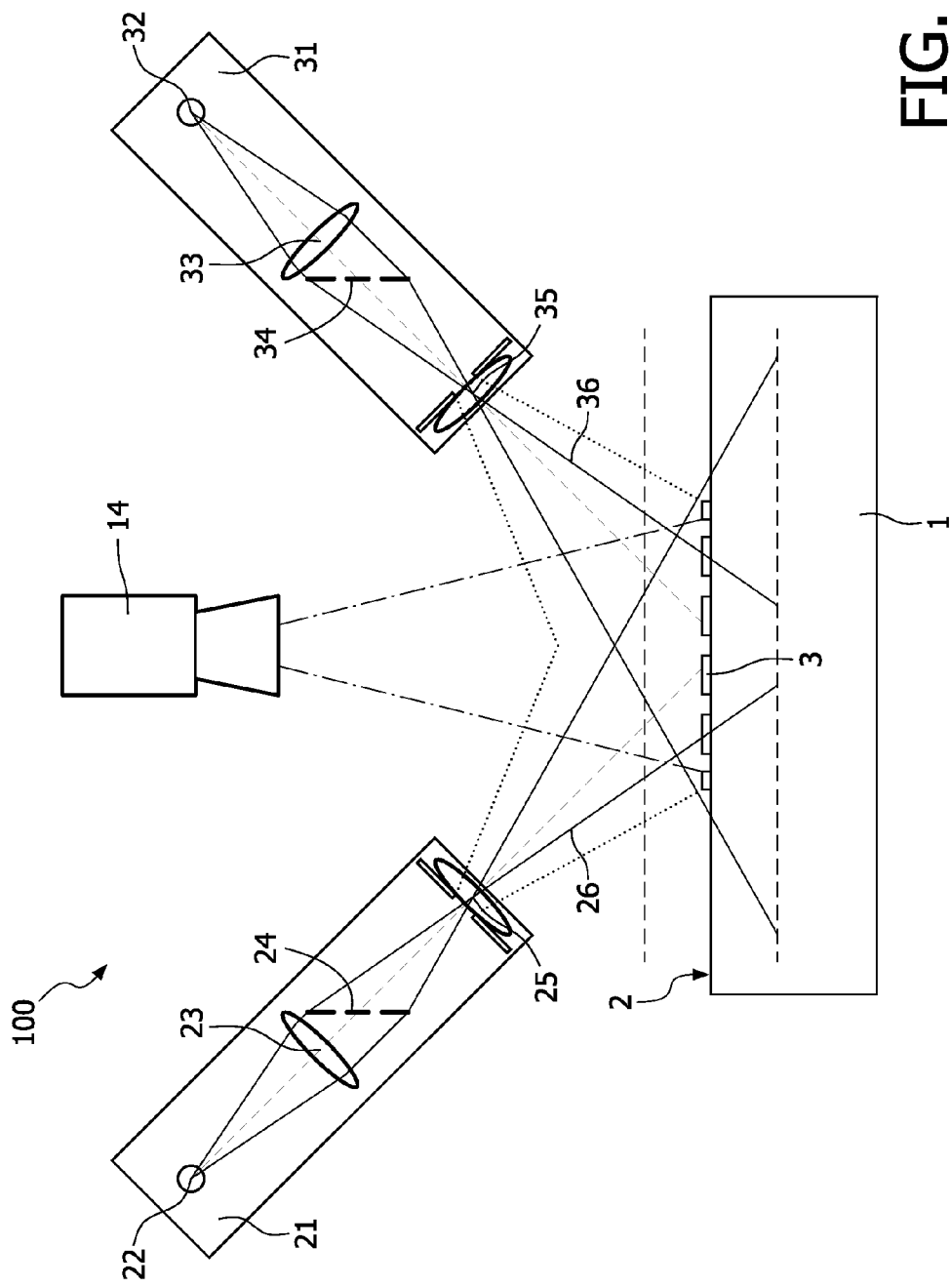
FIG. 1 shows a cross-sectional schematic view of a first embodiment of an apparatus for observing the appearance of the surface of a sample with an optical focus device according to the invention.

FIG. 1 shows schematic cross-sectional view of an apparatus 100 for observing the optical appearance of a sample 1, in this example human skin, having a surface 2 of which a region of interest is to be observed. A camera 14 is present to observe the appearance of the region of interest of the surface 2 of the sample 1. In order to be sure that the region of interest of the surface 2 of the sample 1 is in focus with the camera 14, a first optical focus device 21 and a second optical focus device 31 are available. The first and the second focus device 21, 31 comprise a first and a second focus light source 22, 32 that provide light onto a first and a second focus field lens 23, 33, respectively. The first and the second focus field lens 23, 33 project light onto a first and a second mask 24, 34, respectively, and light that exits the first and the second mask 24, 34 is projected onto a first and a second mask imaging lens 25, 35. The first and a second mask imaging lens 25, 35 provide for a first and a second focus light beam 26, 36, respectively, that project and superpose a first and a second image of the first and the second mask 24, 34, respectively, onto the region of interest of the surface 2 of the sample 1, thereby providing a superposed mask image 3 on the surface 2. The angle of incidence of the first focus light beam 26 is different from the angle of incidence of the second focus light beam 36 as is illustrated in FIG. 1. If the distance between the camera 14 and the surface 2 changes, the superposed mask image 3 will change, because, due to the difference in angle of incidence between the first and the second focus light beam 26, 36, the projected image of the mask 24 will shift along the surface 2 with respect to the projected image of the mask 34. In this way the superposed image 3 is used to quantify if the camera 14 is in focus with the surface 2. The first and the second mask 24, 34 may comprise a pattern of rectangles or circles and may comprise alignment features as are known in the art, such that, when the camera 14 is in focus with the surface 2, a recognizable superposed image 3 results, such as, for example, a rectangle or a circle. Furthermore, if the region of interest of the surface 2 is not normal to the viewing direction of the camera 14, the superposed image 3 will be distorted and will have, for example, not a circular but an ellipsoidal shape. The superposed image 3 can be analyzed manually, i.e. by an operator who operates the apparatus. Alternatively, the superposed image 3 can be analyzed by the camera 14, for example by analyzing the high frequency content of the image, thereby providing for an automatic registration of the focus situation of the camera 14 with respect to the region of interest of the surface 2. Preferably the first and second focus light source 22, 32 comprise blue light. Blue light is preferred above white light because blue light does not penetrate a translucent sample 1, such as human skin, as deeply as white light and thus reduces a blurring of the observed part of the surface 2. Furthermore, the signal to noise ratio of the camera 14, observing the projected image on human skin, is high in the case of blue light, because blue light has a high contrast with the color of the skin.

Figure 2:
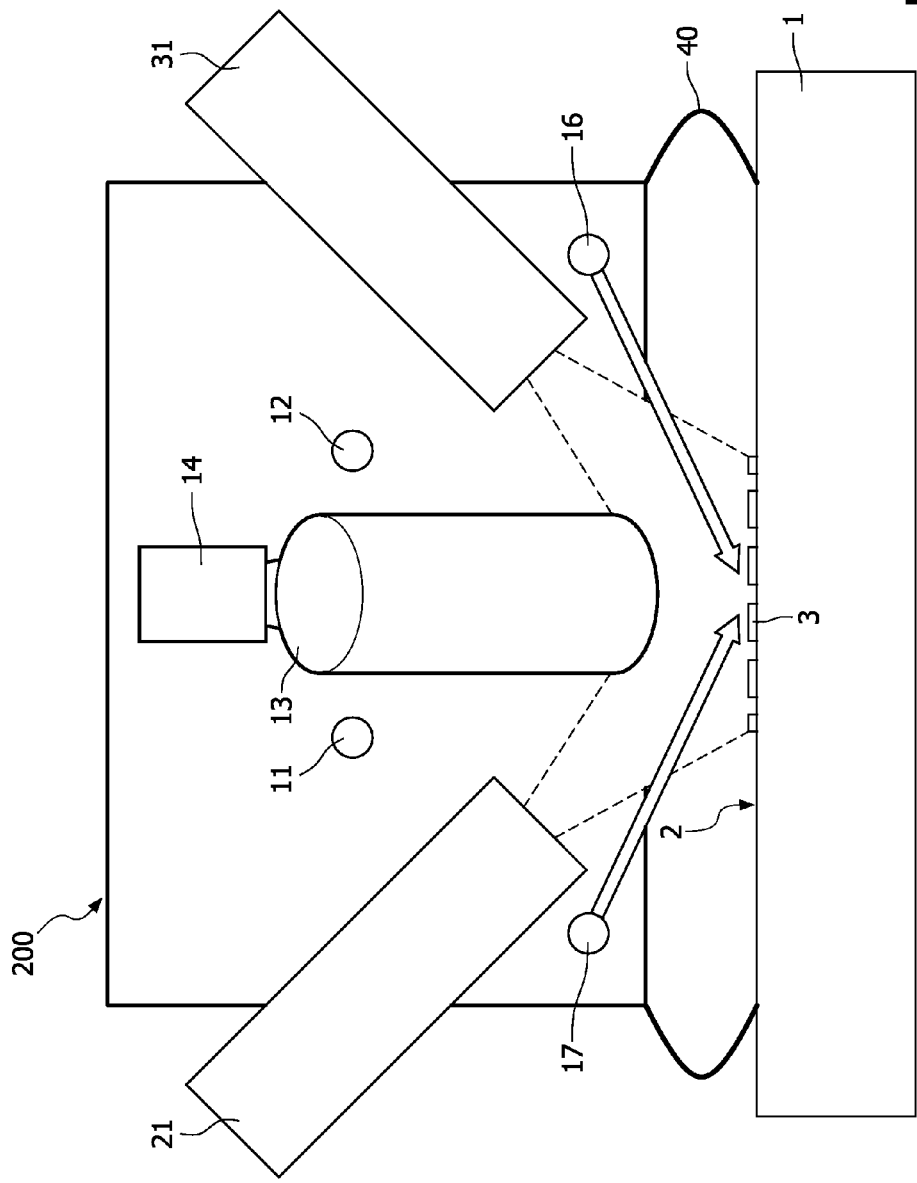
FIG. 2 shows a cross-sectional schematic view of a second embodiment of an apparatus for observing the appearance of the surface of a sample with an optical focus device according to the invention.

In FIG. 2 the principle of a second embodiment of an apparatus 200 according to the invention is shown in a schematic cross-sectional view. In this embodiment the illumination of the region of interest of the surface 2 of the sample 1 is illustrated. The illumination of the sample 1 is, in this embodiment, provided for by near field light sources 11, 12, far field light source 13 and grazing light sources 16, 17. The use of these different illumination light sources is advantageous, because the sample 1 can be illuminated with different illumination parameters, like intensity of the illumination beam, wavelength, collimation and/or angle of incidence of the illumination beam, resulting in a different response beam which is captured by the camera 14. For example, the penetration depth into the surface 2 of the sample 1 is dependent on the wavelength and the angle of incidence of the illumination beam. Due to the different penetration depths of the illumination beams the illumination of the surface 2 of the sample 1 with the different illumination beams, having different angles of incidence, gives access to the surface and the sub-surface areas of the sample 1, wherein the sub-surface areas are different. The response beam, generated at the surface 2 and in the sub-surface areas when using far field light source 13, is measured with the camera 14, which comprises at least one screen and a radiation-sensitive image detection component. Herein the response beam is intercepted by the screen and the two-dimensional image of the screen is captured by the radiation-sensitive detection component and converted into an electric detector signal. The two-dimensional image, formed on the screen, represent the angular distribution of the response beam that is a response of the sample 2 to the illumination with the different illumination beams. The image is therefore a Fourier-like transform of the physical properties of the sample 2, in which a special variation and physical properties of the sample is transformed to an angular variation of radiation energy.

Depending on the illumination beams, which are characterized by the angles of incidence, the Near field, the Far field and/or the Deep field can be detected. The near field describes the image of the surface—what is visible to an observing eye—taken with the radiation-sensitive image detection component. The near field illumination can be used to localize the region of interest before the measurement sequence, including the focus determination, is started. The far field describes how a surface reflects the illumination beam in the distance in angular terms of diffuse scattering, glossy reflections, viewing angle affects and so on. While the result of the far field effects are visible, like gloss, the far field distribution itself is invisible. The far field is captured with the screen forming a two-dimensional image on the screen, wherein the two-dimensional image on the screen is captured by the radiation-sensitive image detection component. The deep field describes how an illumination beam is re-emitted from a translucent material, wherein the response beam is the response from the sub-surface area scattering the illumination beam and re-emitting the response beam from the surface at a location away from an entry point of the illumination beam. Therefore, to measure the deep field, the illumination of a surface with an illumination spot is necessary to obtain the deep field.

FIG. 2 furthermore shows a bellows 40 mounted to the apparatus 200 that contacts the surface 2 of the sample 1. The bellows 40 is flexible and bendable in a direction mainly perpendicular to the surface 2 and is rigid in a direction parallel to the surface 2. In this way the pressure applied to the surface 2 by the apparatus 200 is reduced compared to when a rigid part is applied to touch the surface 2. In the case that the sample 1 comprises deformable human skin, which will bulge and/or discolorize because of an applied pressure which deforms the skin and tends to, at least partly, close off blood vessels giving a different color to the human skin. The bellows 40 advantageously minimize the pressure applied on the skin, and therefore also reduces the negative consequences of a pressure applied to the skin. Another advantage of the bellows 40 is that it shuts off any environmental and unwanted light which may negatively influence the optical observance of the sample 1. The bellows 40 prevents an extra, unwanted and uncontrolled illumination of the sample 1 by environmental light.

Figure 3A:
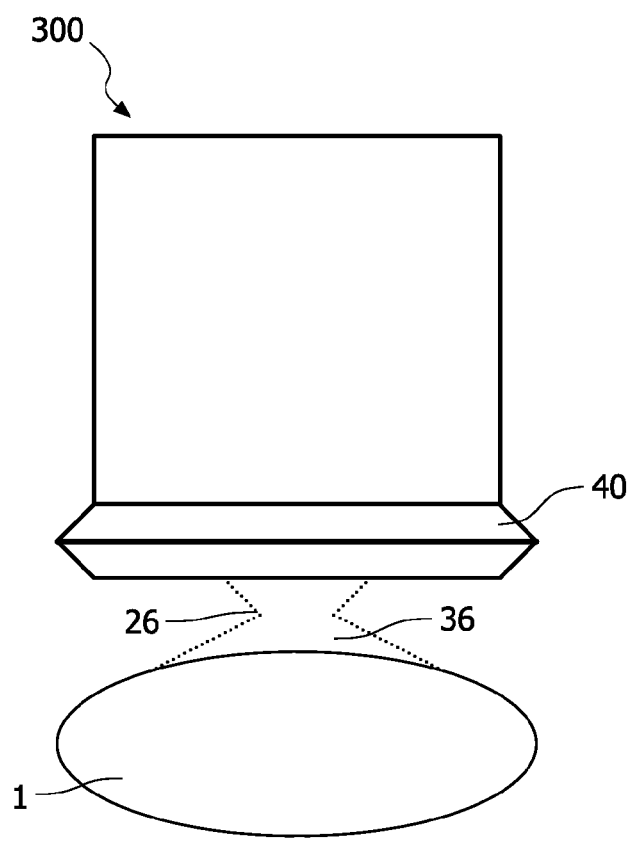
FIGS. 3a and 3b illustrate a method for observing the appearance of the surface of a sample with an optical focus device according to the invention.
Figure 3B:
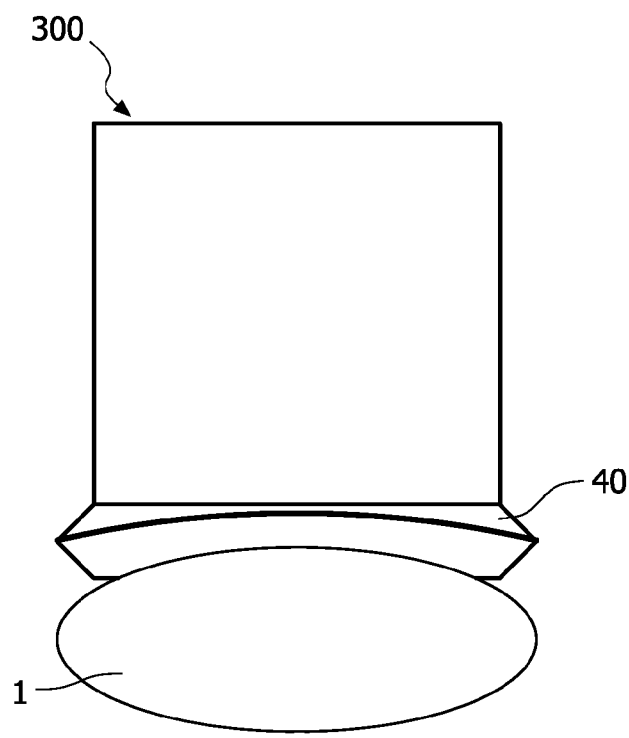

FIGS. 3a and 3b illustrate a method of observing the optical appearance of a sample 1 according to an embodiment of the invention. FIG. 3a shows that the apparatus 300 provides for the first and the second focus light beams 26, 36 which generate the superposed mask image (not shown) on the sample 1. The apparatus 300 is moved towards the sample 1 until the bellows 40 touches the sample 1 and the surface 2 of the sample 1 is in focus with the camera 14 that is inside the apparatus 300, as is illustrated in FIG. 3b. The bellows 40 will deform whereas the sample 1 barely deforms, thereby minimizing the influence of the pressure, applied by the apparatus 300 on the sample 1, on the quality of the optical observance of the sample 1. Now the surface 2 of the sample 1 is in focus with the camera 14, a signal is produced that triggers the start of the observation sequence in which the surface of the sample 1 is illuminated by the different illuminations beams and in which the camera 14 observes the response beam.

Figure 4:
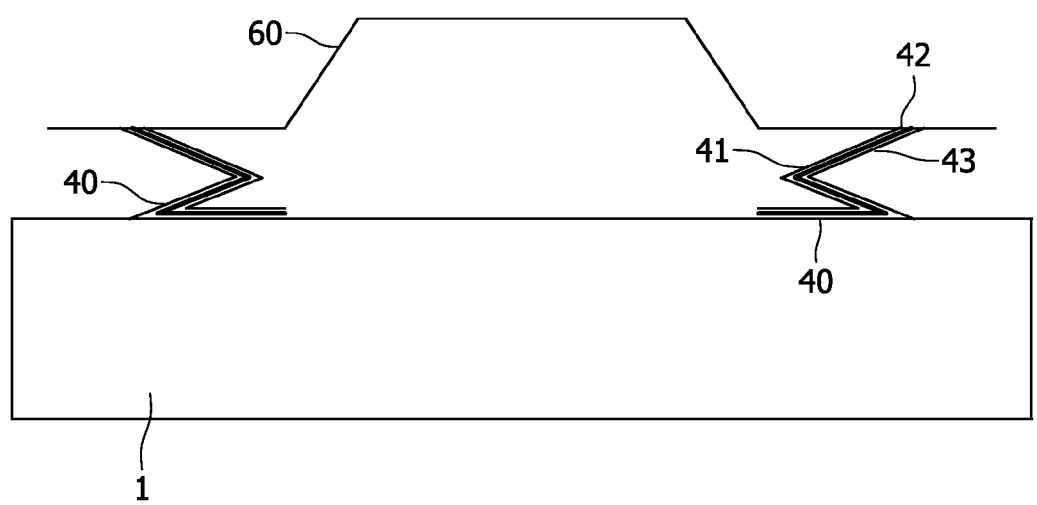
FIG. 4 shows a cross-sectional schematic view of a bellows with a visual contamination indicator according to an embodiment of the apparatus according to the invention.
Figure 5:
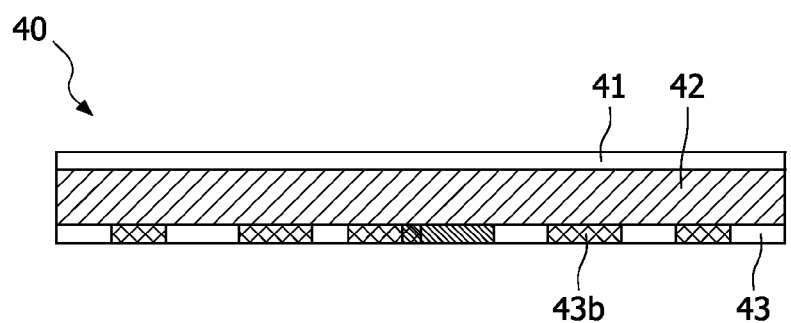
FIG. 5 is a schematic cross-sectional view of a bellows with a visual contamination indicator according to an embodiment of the invention.

FIG. 4 illustrates a part of an embodiment of an apparatus according to the invention showing the bellows 40 touching the sample 1 wherein the bellows 40 is mounted on the apparatus via a transparent cap 60, which comprises, for example, a plastic. The bellows 40 comprises, in this embodiment, three layers. FIG. 5 shows a schematic cross-sectional view of the unfolded bellows 40. The bellows 40 comprises a central layer 42 is made of a material that shuts off external light, such as, for example, black paper. The bellows 40 further comprises a top or inner layer 41, which may have a sticky surface that catches dust particles to prevent these particles to stick to the transparent cap 60. Another advantage of the sticky surface is that it is safeguarded that the bellows 40 is only used once for each sample 1, because after use the sticky surface of the top or inner layer 41 will have parts sticking to each other such that flexed bellows 40 does not return to its original shape automatically. The bellows 40 further also comprises a bottom or outer layer 43 which contacts the surface 2 of the sample 1 and which is of a very light color and is made porous such that it absorbs contaminants, such as oily substances. The absorbance of contaminants in the bottom or outer layer 43 results in discolorizations 43b in the layer 43 on the place of the contaminants. This provides a visual indication of the contaminants on the bellows 40. In this way it is safeguarded that the bellows 40 is only used once for each sample 1 and to replace the contaminated bellows 40 before another sample 1 is measured, thereby preventing cross-contamination between different samples. A stronger discoloration 43b of the layer 43 can be obtained if the central layer 42 is coated with an additional thin layer of a soluble colorant mixed with a hygroscopic agent that dissolves in any skin fluids, or evaporates during a prolonged period of time, and gives a strong coloration of the contact layer 43. The dosing of this colorant must be done carefully so that it cannot reach the skin and leave any marks there.

In summary, the invention relates to an apparatus for observing the optical appearance of a surface of a sample of semitransparent material, in particular the surface of a human skin, the apparatus comprising a light source for illuminating at least a region of interest of the surface of the sample from a predetermined direction, a camera for observing a response to the illumination of the region of interest and an optical focus device for determining if the camera is in focus with the surface of the region of interest. By providing for the optical focus device, the focus point of the camera with respect to the surface of the sample is determined which reduces the negative influence of the mechanical contact of the apparatus with the surface of the sample on the quality of the observance of the optical appearance.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of other elements or steps than those listed in a claim. The word "a" or "an" preceding an element does not exclude the presence of a plurality of such elements.

The invention claimed is:

1. An apparatus for observing the optical appearance of a surface of a sample of a semitransparent material, the apparatus comprising:
    a light source for illuminating at least a region of interest of the surface of the sample from a predetermined direction,
    a camera for observing a response to the illumination of the region of interest, and
    an optical focus device for determining if the camera is in focus with at least a part of the surface of the region of interest,
    wherein the optical focus device provides for a first and a second focus light beam having a first and a second angle of incidence with the surface,
    wherein the first angle of incidence is different from the second angle of incidence,
    wherein the first and second focus light beam provide for a superposition of a first and a second image of a first and a second mask pattern on the surface of the region of interest, and
    wherein the focus is determined by the alignment of the first and the second mask pattern image.

2. An apparatus as claimed in claim 1, wherein the optical focus device comprises a focus light beam which projects a focus image on the surface of the region of interest, wherein the focus image determines if the camera is in focus with the surface of the sample.

3. An apparatus as claimed in claim 2, wherein the focus light beam comprises blue light.

4. An apparatus as claimed in claim 1, wherein the apparatus further comprises measurement means for measuring the alignment of the superposed first and second mask pattern images.

5. An apparatus as claimed in claim 1, wherein the optical focus device triggers the illumination of the region of interest and the observance of the response to the illumination of the region of interest when the camera is in focus with the surface of the region of interest.

6. An apparatus as claimed in claim 1, wherein the apparatus further comprises a deformable contact ring for contacting the surface of the sample on a specific distance from the region of interest and for protecting the surface of the sample from environmental light.

7. An apparatus as claimed in claim 6, wherein the deformable contact ring comprises means for indicating that the deformable contact ring has been used.

8. An apparatus as claimed in claim 7, wherein the means for indicating that the deformable contact ring has been used comprises a visual indicator for contaminants.

9. A method for observing the optical appearance of a surface of a sample of semitransparent material, the method comprising the steps of:
    determining with an optical focus device if a camera, which is on a fixed relative position to the optical focus device, is in focus with at least a part of the surface of a region of interest by changing the distance between the camera, the optical focus device and the surface;
    when the camera is in focus with at least a part of the surface of the region of interest illuminating at least the region of interest of the surface of the sample from a predetermined direction with a light source; and observing a response to the illumination of the region of interest with the camera, wherein the optical focus device provides for a first and a second focus light beam having a first and a second angle of incidence with the surface, wherein the first angle of incidence is different from the second angle of incidence, wherein the first and second focus light beam provide for a superposition of a first and a second image of a first and a second mask pattern on the surface of the region of interest, and wherein the focus is determined by the alignment of the first and the second mask pattern image.

10. A method as claimed in claim 9, further comprising the step of contacting the surface of the sample on a specific distance from the region of interest with a deformable contact ring before the determining step, thereby protecting the surface of the sample from environmental light.

11. An apparatus as claimed in claim 1, wherein the semi-transparent material is the surface of human skin.

12. An apparatus as claimed in claim 9, wherein the semi-transparent material is the surface of human skin.

* * * * *